United States Patent [19]

Yolles

[11] 4,344,431

[45] Aug. 17, 1982

[54] POLYMERIC ARTICLE FOR DISPENSING DRUGS

[75] Inventor: Seymour Yolles, Newark, Del.

[73] Assignee: University of Delaware, Newark, Del.

[21] Appl. No.: 175,309

[22] Filed: Aug. 4, 1980

Related U.S. Application Data

[60] Continuation of Ser. No. 798,535, Dec. 12, 1974, abandoned, which is a division of Ser. No. 102,432, Dec. 29, 1970, Pat. No. 3,880,991, which is a continuation-in-part of Ser. No. 809,946, Mar. 24, 1969, abandoned.

[51] Int. Cl.³ .............................................. A61M 7/00
[52] U.S. Cl. ................................................... 128/260
[58] Field of Search .............................. 128/127–130, 128/260–261, 270, 334, 335.5; 424/19, 22, 108

[56] References Cited

U.S. PATENT DOCUMENTS

| | | | |
|---|---|---|---|
| 2,413,419 | 12/1946 | Saunders et al. | 424/108 |
| 3,042,045 | 7/1962 | Sheridan | 128/349 |
| 3,279,996 | 10/1966 | Long, Jr. et al. | 128/260 |
| 3,312,215 | 4/1967 | Silber | 128/260 |
| 3,426,754 | 2/1969 | Bierenbaum et al. | 128/260 |
| 3,509,877 | 5/1970 | Weiss | 128/260 |
| 3,545,439 | 12/1970 | Duncan | 128/130 |
| 3,618,604 | 11/1971 | Ness | 128/260 |
| 3,880,991 | 4/1975 | Yolles | 128/260 |

OTHER PUBLICATIONS

Amer. J. Obstet. Gyneo. 98(1); 126–7, 1 May 1967, Taubert.

Primary Examiner—C. Fred Rosenbaum
Attorney, Agent, or Firm—Connolly and Hutz

[57] ABSTRACT

An article for dispensing drugs is disclosed which is formed from a crystalline polymeric material having a melting point of at least about 100° C. and a drug. The drug is dispersed throughout the polymer and the combination is formed into a solid shape having structural integrity.

8 Claims, 3 Drawing Figures

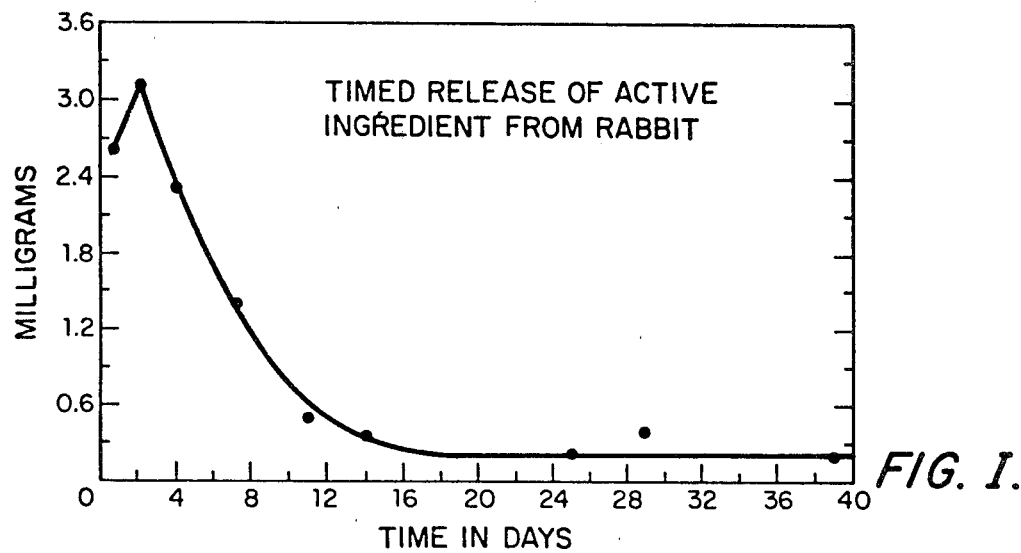
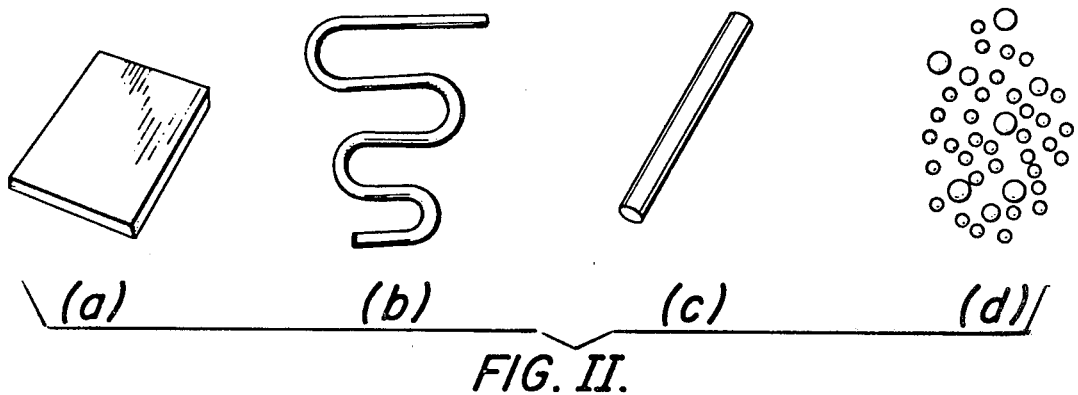
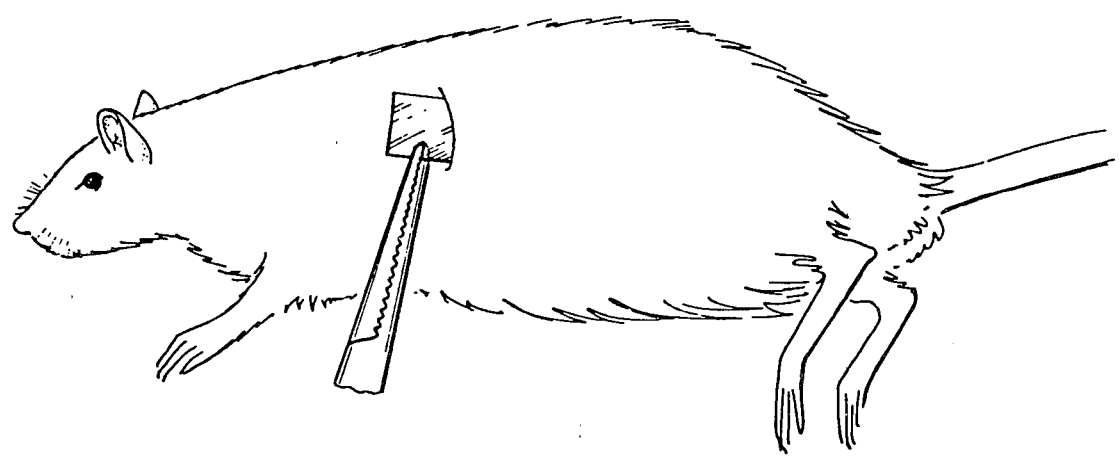

POLYMERIC ARTICLE FOR DISPENSING DRUGS

CROSS REFERENCE TO RELATED APPLICATIONS

This application is a continuation of application Ser. No. 798,535, filed Dec. 12, 1974 now abandoned which, in turn, is a division of Ser. No. 102,432, filed Dec. 29, 1970, now U.S. Pat. No. 3,880,991 and which, in turn, is a continuation-in-part of application Ser. No. 809,946, filed Mar. 24, 1969, and now abandoned.

BACKGROUND OF THE INVENTION

1. Field of the Invention

This invention relates broadly to the controlled release of drugs to the bloodstream of mammals and more particularly to a shaped article formed from a crystalline polymer which contains a drug so that the article is suitable for implantation in a mammal to controllably release the drug.

2. Description of the Prior Art

Medical science has long recognized the need for methods to controllably release therapeutic agents and other drugs to the blood stream fo patients. Recently, a great deal of research has been initiated in attempting to find new release systems to fulfill this need. Several such systems have been recommended.

One common method for obtaining controlled release is to envelop the active substance with coatings which are attacked by digestive juices in the stomach. This technique has been widely used recently for time-release analgesics. There are some problems with this method, however, such as: (1) it is difficult to obtain the proper distribution of coating thicknesses to give the desired release; and (2) the sojourn time of the coated agent in the digestive track is relatively short, thereby making this method unsuitable for long-term release.

Another method of obtaining controlled release is to mix the active substance with various binders such as fats, waxes, and natural or synthetic polymers to slow down release. Many of the binders, however, are unsuitable for use with many drugs. Furthermore, these combinations of binders and drugs tend to disperse quickly after they enter the body due to the binder's solubility in body fluids, the washing effect of the body fluids and/or the attack of digestive juices. After the binder has been so dispersed, all control over the release of the drug is lost.

Other researchers have even suggested that drugs be chemically modified to affect their release and absorption into the bloodstream. The degree of difficulty to this method for obtaining controlled release is clear.

More recently, the possibility of somehow incorporating drugs into polymeric materials to control drug release has been considered. Thus Furuse et al., U.S. Pat. No. 3,514,517, teach that suppositories containing spermicidal agents can be formed by blending the agents with low molecular weight polyethylene glycols; Hill, U.S. Pat. No. 3,458,622, teaches that tablets for controlling the release of medicinal agents for up to eight hours can be formed from a blend of a polymeric vinyl pyrrolidone with a carboxy vinyl hydrophilic polymer; Weil et al., U.S. Pat. No. 3,469,005, teach that drugs for reducing blood pressure in mammals can be incorporated into solid vehicles such as lactose, corn-starch, microcrystalline cellulose, talc, stearic acid, magnesium stearate, gums, etc.; Merabi et al., U.S. Patent 3,495,000, have found that controlled release matrices can be prepared consisting of a dialdehyde starch and ethyl cellulose, polyvinyl chloride or polyvinylpyrrolidone, but that mixtures of the same starches with other pharmaceutically acceptable polymers such as methylcellulose or carboxymethylcellulose do not yield compositions suitable for controlled release; and Herrmann, U.S. Pat. No. 2,155,658, teaches that medical preparations for injection into the body which are flowable above body temperature but solid at body temperature after injection can be made from polymerized vinyl alcohols and their water soluble derivatives and a solvent for such material.

Another technique for incorporating drugs into polymeric matrices is described in Levesque, U.S. Pat. No. 2,987,445 and in Endicott, U.S. Pat. No. 3,087,860. These patents teach a drug dispenser formed from synthetic polymers containing solid particles of a water-leachable drug. Usually the polymer matrix is shaped in the form of a pill which is intended to be orally ingested. This drug dispenser is limited, however, to water-soluble drugs and has relatively short release times, i.e., typically 8–12 hours.

While the above-mentioned patents describe various mixtures of drugs with polymers, Long et al. have taught another method for constructing a controlled release device from polymers in U.S. Pat. No. 3,279,996. Long et al. form a capsule or container from polysiloxane which is intended for implantation. This device has the advantage of making extended time-release treatment possible, but suffers a disadvantage since the possibility exists that the polysiloxane container will develop pinholes or a rupture resulting in an undesired and potentially harmful large amount of drug being released almost instantaneously.

In spite of all of the work being carried on to find suitable polymeric vehicles for dispensing drugs controllably, to date the incorporation of drugs throughout crystalline polymers shaped to various solid forms which have structural integrity after implantation has not been considered.

SUMMARY OF THE INVENTION

It has now been unexpectedly found that an intimate mixture of a drug and a crystalline polymeric material can be formed to a solid, shaped article which will unexpectedly exude the drug to the surface of the polymeric article. For purposes of this description, the term exude is used to mean the migration from the interior of the polymeric material to its surface until the surface is covered with a layer of the drug and an equilibrium is established between the surface layer and the drug at the interior of the polymeric material. If the surface layer is partially or totally removed, the equilibrium is destroyed and further amounts of the drug permeate to the surface until equilibrium is re-established. This cycle will repeat itself until the supply of drug has been exhausted from the polymeric material. The surface layer can be removed in many ways, including but not limited to: rubbing it off; brushing it off; washing it off; dissolving it off; etc.

Relying upon this discovery, a novel article for dispensing drugs has been invented which comprises:

1. a crystalline polymeric material having a high melting point and being formed to a solid shape having structural integrity; and, 2. a drug substantially uniformly and intimately dispersed throughout portions of the polymeric material.

There are many advantages to this drug dispensing device over those previously known. For example, this device provides an economical and reliable method for automatically dispensing controlled quantities of a drug over a short or an extended period of time. Such a device can be implanted within a mammal's body so that it will dispense the required amounts of one or more drugs continuously over extended periods of time without the patient having to rely on periodic injections or oral ingestion of drugs. Once implanted, the dispenser can be forgotten and the patient can rest assured that his body is continuously and automatically receiving the prescribed amount of drug.

A particularly unique advantage of this device is found in the types of therapy where it is desirable to insure that a patient receives a certain amount of a drug, and it is desirable to place control of administering the drug beyond the patient. This obviates the possibility that the patient will forget to administer the drug. It also prevents the patient from deliberately not administering the drug on his own volition, which has heretofore been a serious problem in many types of medical treatment. Once implanted, the drug dispensing devices of this invention are effectively out of the control of the patient.

A most important advantage of the polymeric drug dispenser described herein is the degree of flexibility which can be obtained in administration techniques. As stated above, one suitable method for releasing the drug from this device to a mammals bloodstream is to subcutaneously implant the device. There are many other methods, however. For example, the device can be extruded into the shape of thin "spaghetti" which can be injected into the bloodstream, or the polymeric material can be formed into various sized spheroids for ingestion or injection by a patient. Additionally, the polymeric material can be formed into hollow tubing suitable for catheters. In short, the dispenser of this invention can be formed into limitless solid shapes each suitable for particular methods of controllably releasing a drug to the patient's bloodstream.

BRIEF DESCRIPTION OF THE DRAWINGS

FIG. I is a graphical representation of the controlled release of the steroid progesterone from a device of this invention to the bloodstream of a rabbit;

FIGS. II(a)-(d) are perspective views of some of the variety of shapes of controlled release drug dispensers of this invention;

FIG. III is a perspective view showing the subcutaneous implantation of a controlled release film device of this invention into the back of a rat.

DESCRIPTION OF THE PREFERRED EMBODIMENTS

The polymeric materials used to manufacture the instant device must be crystalline and must have high melting points so that they won't soften when exposed to fairly high temperatures such as those encountered with human body fluids. Preferably the material will have a melting point of 100° C. or more so that the device can be sterilized at high temperatures.

Some examples of suitable polymeric materials include, but are not limited to: polyamides such as nylons; polyolefins such as polypropylene and polyethylene; polyesters such as polyethylene terephthalate; vinyl polymers such as polyvinylidene chloride and polytetrafluoroethylene; polyacetals; cellulose acetate; polypeptides; polycarbonates; polyvinyl ethers and combinations of these.

It has been found that polymers having a crystalline structure yield the most satisfactory control of drug release. Although the reason for this is not known, it may be because of the long segments of linear polymer chains regularly oriented with respect to one another in crystalline polymers. It is known of course, that crystallinity does have a marked effect on physical properties. See Flory, Paul J., *Principles of Polymer Chemistry*, 5th printing, 1966 at pages 49 et seq. It has also been reported in the literature that gaseous diffusion through polymeric membranes is slower, in general, for those polymers having higher degrees of crystallinity than for those with lower degrees of crystallinity. See Michaels, A. S. and Bixler, H. J., "Flow of Gases through Polyethylene and Rubbery Polymers" J. Poly. Sci., vol. 50, 413–39 (1961).

While melting points can be a good indication of polymer crystallinity, the best evidence is obtained by x-ray diffraction patterns.

Some preferred polymeric materials are polyethylene, polytetrafluoroethylene, and polyethylene terephthalate because they are commercially available, economical, and have the required physiological inertness required of any materials considered for implantation into the human body. Polyethylene is particularly preferred.

The crystalline polymeric materials described above have drugs incorporated in them to form the article of this invention. The term drug is used in this description in its broadest sense and covers drugs useful to any mammals including, but not limited to, human beings, wild animals, household animals, and animals raised for their meat or other products such as farm animals and cattle. The term drug is further used in describing this invention to include, but not limited to, the following classes of drugs: (1) therapeutic drugs; (2) preventative drugs; and, (3) diagnostic drugs. It should be understood that a variety of classes, subclasses, and specific examples of drugs not expressly mentioned herein are within the scope of this invention, and these other drugs will be well known or easily ascertainable to those skilled in the art.

Some specific examples of drugs which can be incorporated in crystalline polymers to form a device of this invention are described infra.

As is well known, people suffering from sugar diabetes are required to take daily doses of diabetes control agents. Insulin or the active ingredients in some of the commercially available control agents such as tolbutamide ("Orinase" by Upjohn), chloropropamide ("Diabinese" by Pfizer) and tolazamide ("Tolinase by Upjohn) could be dispensed with an article of this invention.

Many drugs are presently being used to treat rheumatoid arthritis and other forms of arthritis. These include, but are not limited to, narcotic pain relievers, gold salts, corticosteroids, adrenocorticotropic hormones, phenylbutazone and its derivatives, antimalarials, and indole derivatives. A comprehensive listing of specific drugs used to treat the various forms of arthritis is given in the Aug. 12, 1968 edition of *Chemical and Engineering News* at pages 54 and 55, which listing is herein incorporated by reference. These drugs could be dispensed with the instant article.

Antibiotics are a further group of drugs which can be dispensed. Some examples of suitable antibiotics include the tetracyclines, penicillan, streptomycin, and aureomycin.

Deworming and distemper drugs such as those given to household pets and/or cattle are another group of drugs capable of being dispensed by the device of this invention. An example of such a drug is phenothiazine.

Sulfur drugs such as sulfisoxazole diolamine ("Gantrisin" by Roche Laboratory), useful in treating urinary tract infections, could also be exuded from a crystalline polymeric article.

Another group of drugs suitable for use in the crystalline polymeric articles are the cancer-control agents. An example would be the drugs or combinations of drugs useful for treating leukemia such as the nitrogen mustard p-(di-2-chlorethyl)-amino-phenylbutyric acid.

Two further groups of drugs which could be advantageously dispensed with the hereindescribed device are alcohol-addiction control agents and tobacco-smoking addiction control agents.

Closely related are the addictive drug antagonists. If an addictive drug such as heroin, morphine, codeine, neopine, etc. is taken while the blood still contains the antagonist, the addictive drug will pass through the body and be harmless to the taker in the sense that the taker will not experience "a high" and the drug will not be addictive. Such antagonists have offered a very successful method for treating drug addicts while the addicts are at clinics; however, it has been noted that once addict returns to his original environment, and is out of control of the clinic, he is likely to stop taking the antagonist and resume taking one of the addictive drugs. For this reason, the article of this invention offers unique advantages in treating drug addicts by this method since such an article containing an antagonist could be implanted within the addict's body, thereby giving him no control over the administering of the antagonist. This will extend the addict's period of cure beyond the time that he can actually be confined to a clinic. Some examples of specific drug antagonists suitable for incorporation into the polymeric dispenser include N-allyl-noroxymorphone ("Naloxone") and 2-cyclopropylmethyl-2'-hydroxy-5, 9-dimethyl-6,7-benzomorphone ("Cyclazocine"). Other drug control agents such as "Methadone" can also be used.

Two further groups of closely related drugs are the thyroid gland regulating drugs and weight-control drugs. Here again, there is a particular advantage to the use of the polymeric dispenser since such a device can be implanted within the body of the patient and thereby supply the required amount of drug without the patient having any control over this. Also, it is known that these types of drugs are extremely dangerous when taken in large doses, and the use of this device would help assure that an overdose did not get into the patient's bloodstream.

Another group of drugs which could be dispensed are the analgesic drugs. These drugs have little or no therapeutic effect, but serve to lessen or eliminate the severe pain often encountered with many diseases or operations. For example, in the cases of chest cancer, morphine or codeine are often prescribed. Also, for patients suffering from cancer of the prostate glands, progesterone is often prescribed. One particularly advantageous use of the polymeric dispenser would be in serious surgical operations which result in severe pain to the patient after the operation is completed and the patient regains consciousness. In these cases, the body is going to be opened for the operation, and a device of this invention containing a pain killer could be inserted into the body during the operation to ease the pain to the patient during the recovery period. Of course, there are many other types of analgesic drugs and many other examples of when such drugs could be used which will be apparent to those knowledgeable in the field of medicine.

Another group of drugs suitable for being dispensed from the polymeric article are the hormone-regulating drugs to aid fertilization or to act as contraceptives. One preferred embodiment using hormone-regulating drugs is formed using the active ingredients in oral contraceptives. The advantage is that a device containing the active ingredients of oral contraceptives could be designed to last over extended periods of time thereby relieving the taker from a daily routine of orally taking the contraceptives. Suitable examples of the active ingredients in oral contraceptives include a progestin or a combination of a progestin and an estrogen. For example, a homogeneous dispersion of the active ingredient in "Norethindrone" and "Mestranol" in a ratio of 20:1 by weight could be prepared and incorporated into the solid polymeric material. Other examples of synthetic progesterones and estrogens suitable for use with this invention include: Norethynodrel, Medroxyprogesterone acetate, Dimethisterone, Ethynodiol diacetate, Chlormadinone acetate, Norethindrone acetate and Ethynylestradiol.

One particular advantageous embodiment is the combination of an intrauterine device and the article of this invention. This can be prepared by forming a suitable polymeric material containing an oral contraceptive into the shape of an intrauterine device. The device could then be inserted into the uterus of a woman and would offer the double protection of the exuding oral contraceptive and the intrauterine device principle. The intrauterine device could have any shape including, but not limited to, a spiral, bow, loop, ring, coil, or trefoil. Besides using contraceptive combinations of steroids in such a device, it would also be possible to use a spermicidal agent such as the terpenylphenyl polyoxyethylene ethers described in Furuse, U.S. Pat. No. 3,514,517.

Other drugs which can be incorporated in the systems of this invention include: drugs for reducing blood pressure such as those described in U.S. Pat. No. 3,469,005; pharmaceutical compositions for the control of appetite such as the combinations of amphetamines and thioridazines described in U.S. Pat. No. 3,495,005; and, agents for treating psychosis in mammals such as those described in U.S. Pat. No. 3,495,007.

The above listing of drugs is not intended to be comprehensive, but merely representative of the wide variety of drugs which can be used with this invention. Those skilled in the art will know or be able to determine by routine experimentation that many other specific drugs are also suitable.

The amount of drug dispersed in the polymeric article will depend, of course, on many factors including the specific drug, the function to be accomplished, the length of time it is desired to dispense the drug, the amount of drug to be dispensed in a specified time, the size of the device, and many other factors. In general, amounts ranging from about 0.5% to about 50% by weight of the polymeric material can be incorporated. Particularly good results can be obtained with from at least about 10% to about 20%, The amount of drug to be dispensed in a specified time, will of course, depend on such factors as the particular application, the particular drug, the age of the patient, etc. In general, what will constitute an "effective amount" will be known or easily ascertainable by those skilled in the art. Much of this type of data is published in the literature or easily determined by routine experimentation. Examples of the published literature on effective amounts of progestin-type steroids, in this case for topical application, can be found at: Shipley, "Effectiveness of Topical Application of a Number of Progestins", *Steroids* 5(5): 699–717, May, 1965; and Ringler, "Efficacy of Topically Applied Progestational Agents", *Steroids* 7 (4): 341–349, April, 1966. In a like manner, the following literature describes effective amounts of addictive drug antagonists: Martin, W. R., "Opioid Antagonists", *Pharmacological Reviews,* vol. 19, no. 4, pages 463–521 (1967) and references contained therein; Freedman, A. M., "Cyclazocine and Methadone in Narcotic Addiction", *The Journal of the American Medical Association,* Oct. 16, 1967, vol. 202, pages 191–194. Also, the patents mentioned above often contain data on effective amounts for any particular application.

The dosage administered by this dispenser can be controlled by the size and shape of the article, concentration of the drug in the polymer, surface area, pore size, matching of the polymer and drug, nature of the surroundings, etc. This is a particular advantage where it is desirable to deliver a metered amount of the drug over a specified period of time.

Of course, combinations of drugs and substances in addition to drugs can also be incorporated into the polymeric material. For example, radioactive tracers such as carbon-14, nonradioactive tracers such as barium sulfate, carriers which would transport the drug through skin such as dimethylsulfoxide and dimethylsulfone, water-soluble excipients, etc. could be incorporated with certain drugs for particular applications. The amount of auxiliary agent used will depend, of course, on the specific agent, drug and polymer used to fabricate the article as well as the purpose for incorporating the auxiliary agent.

As has been described, the polymeric article dispenses the drug it contains by exuding it to the surface of the article. The mechanism of how the drug enters the body from the polymer surface is not critical and can be accomplished with a variety of techniques. For example, the article may be placed upon a person's body in contact with the skin so that the particular drug could be absorbed through the person's skin into the bloodstream. An alternative technique is to implant the device within the patient's body at a location where the surface layer of drug will be in contact with any of the various body fluids or tissue so that the drug could be dissolved and/or carried away by such body fluids or rubbed off and absorbed by the tissue. Subcutaneous implantation of a film drug dispenser under the skin on the back of a rat is shown in FIG. III; a more detailed description of such implantation techniques is presented in the examples. Intramuscular implantation is also contemplated. Still another technique would be to prepare the article for use in the patient's mouth so that the saliva would carry the drug into the body. In certain cases, it might be advantageous to insert the dispenser in other body cavities such as the uterus. Other techniques for getting the material from the surface of the article into the body will be readily apparent to the medical profession.

The dispensing articles described herein can be formed by pre-mixing the polymer, drug and any auxiliary agents to be incorporated with the drug and then following conventional techniques to shape and set the article. For example, the polymer and drug can be mixed together in a suitable solvent until a homogeneous solution is formed. After driving off solvent, the residue can be molded, extruded, etc. to the desired shape. Another method of forming the dispenser might be to compact at elevated pressures a dry mixture of drug and polymer. Also, monomer and drug can be mixed with subsequent polymerization of the monomer.

Another method of forming the drug dispensers is to soak a previously shaped piece of polymeric material in a solution of the drug to be incorporated, and subsequently drying the surface of the article. This technique must be distinguished, however, from simply dipping a polymeric article in a solution to coat the surface of the article with a substance. In the soaking technique of this invention, the conditions, i.e. solvent, polymer, temperature, etc., must be carefully chosen to insure that the active ingredient penetrates deeply into the polymer matrix instead of remaining only on the surface or penetrating a small distance below the surface as a coating does. One way to accomplish the desired deep penetration is to choose a solvent which causes the polymer to swell in the solution of drug. Some solvents cause swelling at room temperatures; others require elevated temperatures. Once the polymer has swollen, solvent and active ingredient can penetrate deeply into the polymer matrix. With rapid cooling, the polymer returns its non-swollen condition trapping solvent and active ingredient within it. If the solvent chosen is highly volatile, while the active ingredient is not, the solvent can be driven out of the article by continuous pumping, i.e. exposing the article to reduced pressures. Those skilled in the art will be able to select appropriate conditions for carrying out this technique.

Other methods for making the polymeric dispensing articles will be apparent to those skilled in the art.

An important feature of the dispenser, which results from the way it is prepared, is that there is a substantially intimate dispersion of drug throughout polymer. This is to be contrasted with a foraminous plastic matrix containing discrete solid particles of a drug only within the voids, such as described in U.S. Pat. Nos. 2,987,445 and 3,087,860. In these patented systems, drug release is predicated upon water or other liquids leaching the drug from the voids; in the dispenser of this invention, drug release is predicated upon exudation of the drug to the polymer surface.

Another important feature of the dispenser, which also results from the way it is prepared, is that the dispenser has "structural integrity". This means that the shaped dispenser will remain intact after prolonged exposure to body fluids. Although it is difficult to list all of the factors which contribute to the structural integrity, some include: substantial non-solubility and non-swellability in water or body fluids; relatively high tensile strengths; and good elongation at break and tensile modulus. Additionally, the polymeric matrices of this invention do not soften appreciably at temperatures as high as 100° C. as many of the prior art waxy binders do.

A test to establish structural integrity is as follows. The shaped drug carrier is immersed in distilled water at 37° C. for 7 days. After this period, weight loss of carrier and dimensional changes of carrier should be less than 10% of their original values. The polymeric matrices of this invention meet this test.

The shape of the dispenser will depend on its intended use. Any shape is within the scope of this invention. Some possible and preferred shapes are illustrated in FIG. II wherein (a) illustrates a film, (b) illustrates a contraceptive intrauterine device known as the Lippes Loop, (c) illustrates a piece of hollow tubing suitable for implantation or for use as a catheter, and (d) illustrates various sized solid spheroids which could be injected into a patient or orally ingested by the patient. Other shapes contemplated but not shown include solid "sphagetti-like" and "fiber-like" configurations and a mesh configuration which would be expected to minimize the possibility of a device subcutaneously implanted causing blood clotting.

The drug dispenser can also be shaped as a body organ or any part thereof. For example, an artificial heart valve could be formed from a polymer containing a drug which would lessen rejection of the new valve. Those skilled in the art will know many other organ shapes to which the drug dispenser could be formed.

As is evident from the forgoing discussion, the article of this invention has many uses, all of which fall within the general utility of dispensing drugs to mammals.

The following examples serve to further illustrate the invention. All parts and percentages are by weight, unless otherwise specified.

EXAMPLE I

A Woman's Intrauterine Device Molded from Polyethylene Resin Impregnated with an Effective Amount of a Contraceptive Progestin and Estrogen Combination Eighty parts of polyethylene resin as fine powder is dissolved in 320 parts of boiling toluene. Twenty parts of a mixture of norethindrone (19.048 parts) and mestranol (0.952 parts) is added slowly with stirring to the refluxing polyethylene-toluene solution. When the solution has cleared indicating homogeneity, the volatile solvent toluene is removed by flash distillation at reduced pressure. The residue consists of an intimate dispersion of norethindrone-mestranol in polyethylene. The hot, semi-solid mass is formed into solid shapes having the geometry of any of the well-known intrauterine devices by conventional polyethylene molding techniques. Each is suitable for intrauterine insertion into the uterus of a woman to dispense effective amounts of the norethindrone-mestranol contraceptive combination. Analysis of a device reveals that the composition consists substantially of 80 parts polyethylene and 20 parts of a mixture of norethindrone and mestranol.

To demonstrate that a contraceptive combination of drugs could be released, polyethylene implants prepared as described above except shaped as films instead of IUD's were subcutaneously implanted into the backs of rabbits. Trace amounts of radioactive tagged ingredients were used with the norethindrone-mestranol combination. Measurements of the disintegrations per minute with scintillation counting equipment of samples of rabbit blood and urine demonstrated that effective amounts of the contraceptive combination were being released from the device to the rabbits bloodstream.

EXAMPLE II

Flexible Polyethylene Tubing Containing an Addictive Drug Antagonist

Eighty parts of polyethylene resin as ⅛ inch cubes and 20 parts of N-allyl-noroxymorphone are blended on a steam heated two-roll rubber mill. This mixture is then placed in a conventional twin screw extruder and extruded into flexible tubing of 1/16 inch diameter. This tubing can be subcutaneously implanted into various parts of a drug addict's body, and when so implanted will release the N-allyl-noroxymorphone to the addict's bloodstream. Alternatively, the tubing could be extruded as a hollow catheter and implanted by catheterization techniques.

EXAMPLE III

Polyethylene Film Implants Containing Progesterone

Eight grams of powdered polyethylene resin and two grams of progesterone together with a trace of radioactive tagged progesterone are dissolved in 250 milliliters of hot xylene. The clear solution is evaporated down to about one-half of its original volume and the remainder is poured onto glass plates where the solvent is allowed to evaporate. The remaining solid mixture is placed in an oven at 100° C. for two hours to drive off remaining solvent.

Films are formed by placing the dried solids between two sheets of aluminum foil and pressing at 150° C. and 5,000 p.s.i. for five minutes in a Carver press. The films are formed with a circular shape having a diameter of 3–4 inches and a thickness of 5 to 6 mils. If desired, the pressing technique is repeated to make the films more uniform.

A polyethylene film prepared as described above was cut into one-inch squares. Four of these one-inch squares were subcutaneously implanted into the backs of four rabbits. Each film section weighed approximately 250 milligrams and contained about 50 milligrams of progesterone. After implantation, the rabbits were placed into metabolism cages.

Release of progesterone into the blood stream of the rabbits was monitored by radioactive counting of blood samples taken periodically from the hearts and 24-hour urine samples. The release of progesterone for one rabbit is shown in FIG. I plotted as milligrams of active ingredient delivered per day.

Table I presents the initial and final rabbit weights for the period of testing, the implant weights, and the radioactive count of blood samples 48 hours after implantation. As can be seen from the radioactive count of blood samples, the progesterone was being released by the implant to the rabbit's bloodstream.

Table II presents progesterone release data obtained from the urine samples collected. As can be seen, each of the rabbits was receiving daily dosages of progesterone from the implant over the period of testing.

After the test period, each of the four rabbits was killed by intracardiac injection of 1,1,1-trifluoro-2-bromo-2-chloroethane. The implants were recovered by dorsal incision, inspected and placed as found into paper envelopes. There was very little visible tissue reaction Small amounts of clear fluid were found in the "tissue" pouch around the implant.

The removed implants were weighed and subsequently dissolved in xylene so that a final radioactive count and weight loss after 60 days could be checked. The results are shown in Table III.

TABLE I

| Rabbit | Initial Rabbit Weight, kg. | Implant Weight, gm. | DPM*/ml. of blood after 48 hours. | Final Rabbit Weight After 43 days, kg. |
|---|---|---|---|---|
| A | 2.14 | 0.2488 | 8 | 3.5 |
| B | 2.18 | 0.2500 | 5 | 3.4 |
| C | 1.84 | 0.2592 | 34 | 3.2 |
| D | 1.94 | 0.2103 | 14 | 3.1 |

*disintegrations per minute

TABLE II

URINE COUNTS, ACCUMULATED DPM

| PERIOD: | 24 hr. | 48 hr. | 96 hr. | 7th day | 11th day | 14th day | 25th day | 29th day | 39th day |
|---|---|---|---|---|---|---|---|---|---|
| Rabbit: A | 172,393 | 376,199 | 680,383 | 961,818 | 1,101,648 | 1,177,648 | 1,373,998 | 1,473,468 | 1,624,768 |
| B | 198,700 | 475,055 | 820,913 | 1,136,913 | 1,495,473 | 1,665,123 | 2,089,688 | 2,218,680 | 2,507,576 |
| C | 174,948 | 471,468 | 839,004 | 1,095,092 | 1,356,887 | 1,479,131 | 1,691,631 | 1,742,931 | 1,825,321 |
| D | 118,779 | 356,046 | 657,966 | 924,973 | 1,136,023 | 1,283,723 | 1,530,788 | 1,673,977 | 1,809,127. |

% Delivered Calculated from Radioactive Count after 39 Days

A—47.5%
B—73.5%
C—53.5%
D—53.0%

TABLE III

| Rabbit | Final Implant Weight, gm. | Residual Count After 60 days, DPM | % Active Ingredient Delivered By Weight Method 60 days | % Active Ingredient Delivered By Residual Count Method 60 days |
|---|---|---|---|---|
| A | 0.2056 | 452,000 | 86.8 | 86.7 |
| B | 0.2059 | 527,000 | 88.2 | 84.5 |
| C | 0.2130 | 835,000 | 89.1 | 76.4 |
| D | 0.1730 | 458,000 | 88.7 | 84.0. |

EXAMPLE IV

Polyethylene Film Implant Containing the Drug Antagonist Cyclazocine

A subcutaneous implant in the form of polyethylene film is prepared as in Example III except that 20% cyclazocine with a trace of radioactive tagged cyclazocine is used as the active drug. Cyclazocine is an addictive drug antagonist.

Pieces of a film prepared as above were cut into two centimeter square areas. Some pieces were weighed, combusted and radioassayed to provide a measure of the concentration of radioactivity present in each piece. Other pieces of the same film were implanted subcutaneously in the backs of rats under light ether anesthesia. The stab wounds were sutured and remained so until the end of the experiment at which time the wounds were reopened and remaining implants were removed for final radioassay.

The rats were placed in Acme metabolism cages for 62 days for the spearation and collection of urine and samples. Total daily urinary radioactivity was measured daily for the first ten days and every four days thereafter. This was accomplished by liquid scintillation techniques and the data was reported as "% of dose excreted per day" and also as "cumulative % of dose". The final radioassay indicated that all of the cyclazocine was released from each device in each rat. The results are presented in Table IV.

TABLE IV

% CYCLAZOCINE RELEASED, CUMULATIVE

| Day | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| Rat A | 11.0 | 15.1 | 19.6 | 21.5 | 25.7 | 27.7 | 30.2 | 48.4 | 50.2 | 51.6 | 52.7 | 53.8 | 54.9 | 56 | 56.4 | 56.8 | 47.2 | 57.6 | 58.6 | 59.6 |
| B | 7.6 | 11.6 | 13.6 | 15.5 | 17.4 | 18.7 | 19.3 | 21.0 | 24.3 | 26.5 | 27.2 | 27.9 | 28.6 | 29.3 | 30.1 | 30.9 | 31.7 | 32.5 | 33.6 | 34.7 |
| C | 11.5 | 16.7 | 19.3 | 20.0 | 21.5 | 23.7 | 24.8 | 25.9 | 27.0 | 28.5 | 30.0 | 31.5 | 33.0 | 34.5 | 35.6 | 36.7 | 37.8 | 38.9 | 40.0 | 41.1. |

RAT AND IMPLANT DATA

| | Initial Rat Weight, gm. | Initial Implant Weight, gm. | Initial DPM |
|---|---|---|---|
| Rat A | 675 | 0.1312 | 268,960 |
| B | 590 | 0.1377 | 282,285 |
| C | 680 | 0.1304 | 267,000. |

EXAMPLE V

Implant Prepared From a Polylactide Film Containing Cyclazocine

Six grams of polylactide with a molecular weight of about 40,000 prepared from L(−) lactide according to Example I of British Patent Specification No. 1,040,168 is dissolved in 250 milliliters of chloroform. Three grams of tributylcitrate and 2.25 grams of cyclazocine are added to the hot stirred solution. This is followed by the addition of five milliliters of a trace of radioactive cyclazocine to monitor drug release. The solution is evaporated to about one-half its original volume and poured onto glass plates. The residue on the plate is air-dried for 20 minutes and oven-baked at 100° C. for one-half hour. Films are prepared by pressing the dried material between sheets of aluminum foil on a Carver press at 140° C., 135° C., and 130° C., all at 10,000 p.s.i.

Samples of films prepared in this manner were implanted into the backs of rats and cyclazocine release was monitored by radioassay. Implant and radioassay techniques were the same as those described in Example IV.

The results are presented in Table V.

TABLE V

% CYCLAZOCINE RELEASED, CUMULATIVE

Film Pressed at 140° C.

| Day: | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| Rat: D | 6.9 | 11.9 | 14.9 | 16.1 | 17.0 | 18.0 | 18.7 | 19.4 | 20.0 | 20.7 | 21.0 | 21.3 | 21.6 | 21.9 | 22.2 | 22.5 | 22.8 | 23.1 | 23.4 | 23.7 |
| E | 4.4 | 7.7 | 9.2 | 10.5 | 11.6 | 12.3 | 13.5 | 14.3 | 15.4 | 16.7 | 17.3 | 17.9 | 18.5 | 19.1 | 19.3 | 19.5 | 19.7 | 19.9 | 20.1 | 20.3 |
| F | 0.8 | 4.1 | 6.1 | 7.5 | 9.3 | 10.5 | 11.3 | 12.3 | 13.3 | 14.1 | 14.6 | 15.1 | 15.6 | 16.1 | 16.6 | 17.1 | 17.6 | 18.1 | 18.3 | 18.5 |

Film Pressed at 135° C.

| Day: | 1 | 2 | 3 | 4 | 5 | 6 | 7 | 8 | 9 | 10 |
|---|---|---|---|---|---|---|---|---|---|---|
| Rat: G | 38.0 | 63.6 | 76.9 | 78.4 | 80.8 | 81.5 | 81.8 | 82.2 | 82.4 | 82.5 |
| H | 17.0 | 32.0 | 39.3 | 45.1 | 50.0 | 53.6 | 56.8 | 60.2 | 63.4 | 65.9 |
| I | 14.0 | 24.3 | 25.3 | 28.2 | 32.1 | 34.6 | 37.7 | 40.1 | 41.5 | 42.5 |

Film Pressed at 130° C.

| Day: | 1 | 2 | 3 | 4 | 5 | 6 | 7 | 8 | 9 | 10 |
|---|---|---|---|---|---|---|---|---|---|---|
| Rat: J | 30.7 | 62.4 | 81.9 | 89.0 | 89.5 | 89.8 | 90.0 | 90.2 | 90.5 | 91.7 |
| K | 15.2 | 37.0 | 58.6 | 75.5 | 83.8 | 84.6 | 84.8 | 84.9 | 85.1 | 85.8 |

RAT AND IMPLANT DATA

| | Initial Weight gm. | Initial Implant Weight, gm. | Initial DPM |
|---|---|---|---|
| Rat D | 645 | 0.0671 | 1,970,000 |
| E | 520 | 0.0708 | 2,080,000 |
| F | 350 | 0.0732 | 2,150,000 |
| G | 690 | 0.0512 | 1,475,000 |
| H | 670 | 0.0548 | 1,580,000 |
| I | 530 | 0.0690 | 1,990,000 |
| J | 520 | 0.0791 | 2,070,000 |
| K | 580 | 0.0942 | 2,450,000 |

What is claimed is:

1. An article for controllably dispensing drugs, comprising:
    a. crystalline polyethylene having a melting point of at least 100° C. formed into a solid shape which has structural integrity; and
    b. from about 0.5% to about 50% by weight based on said polyethylene of an addictive drug antagonist present in an antagonistically effective amount and substantially uniformly and intimately dispersed throughout portions of said shaped polyethylene with an outer surface of said solid shape comprising means for diffusing said drug antagonist therethrough with said drug antagonist exuding to said outer surface.

2. A controlled release drug dispenser comprising an intimate mixture of crystalline polyethylene having a melting point of at least about 100° C. and an addictive drug antagonist present in an antagonistically effective amount, said mixture being formed into a solid shape having structural integrity.

3. In the art of administering effective amounts of an addictive drug antagonist to a taker of an addictive drug which can be taken while the blood still contains the antagonist, the improvement which consists essentially of the steps of subcutaneously implanting in the body of an ambulatory, nonconfined drug addict a shaped article having structural integrity, said shaped article being formed from a crystalline polymeric material having a melting point of at least about 100° C., said article having dispersed therein an effective amount of an addictive drug antagonist, thereby extending the ambulatory, nonconfined addict's period of cure beyond the time of actual clinical confinement.

4. An improvement of claim 3 wherein said polymeric material comprises polyethylene.

5. In the art of contraception by means of an intrauterine device, the improvement which consists essentially of the step of offering the added protection of an exuding contraceptive drug in effective amounts by inserting into the uterus of a woman an intrauterine device formed from a crystalline polymeric material having a melting point of at least about 100° C., said crystalline polymeric material having intimately dispersed therethrough an effective amount of a contraceptive drug.

6. An intrauterine device comprising:
    a. a crystalline polymeric material formed into the shape of an intrauterine device; and,
    b. a contraceptive drug uniformly and intimately dispersed throughout said intrauterine device, said drug being present in an effective contraceptive amount.

7. An intrauterine device of claim 6 wherein said contraceptive drug comprises an estrogen or a progestin or a combination of an estrogen and a progestin.

8. An intrauterine device of claim 6 wherein said contraceptive drug comprises a spermicidal agent.

* * * * *